United States Patent [19]

Senturia et al.

[11] 4,317,084
[45] Feb. 23, 1982

[54] OSCILLATOR THAT INCLUDES A CHARGE-FLOW TRANSISTOR

[75] Inventors: Stephen D. Senturia, Boston; Kou Togashi, Cambridge, both of Mass.

[73] Assignee: Massachusetts Institute of Technology, Cambridge, Mass.

[21] Appl. No.: 76,038

[22] Filed: Sep. 17, 1979

[51] Int. Cl.³ .............................................. H03B 25/00
[52] U.S. Cl. ....................................... 331/57; 331/65; 357/25
[58] Field of Search ...................... 331/57, 111, 65, 66, 331/108 D, 113 R, 135, 143; 357/25, 23, 26, 41

[56] References Cited

U.S. PATENT DOCUMENTS

| | | | |
|---|---|---|---|
| 3,351,871 | 11/1967 | Swain | 331/57 |
| 4,158,807 | 6/1979 | Senturia | 324/71 SN |
| 4,209,796 | 6/1980 | Senturia | 357/25 |
| 4,236,121 | 11/1980 | Senturia | 357/25 |

Primary Examiner—David K. Moore
Attorney, Agent, or Firm—Arthur A. Smith, Jr.

[57] ABSTRACT

An oscillator having a logic element that includes a charge-flow transistor and a load element, in combination, and that further includes a Schmitt trigger or the like connected to receive as input thereto an output from the logic element and to provide an output that is fed back as input to the logic element.

14 Claims, 9 Drawing Figures

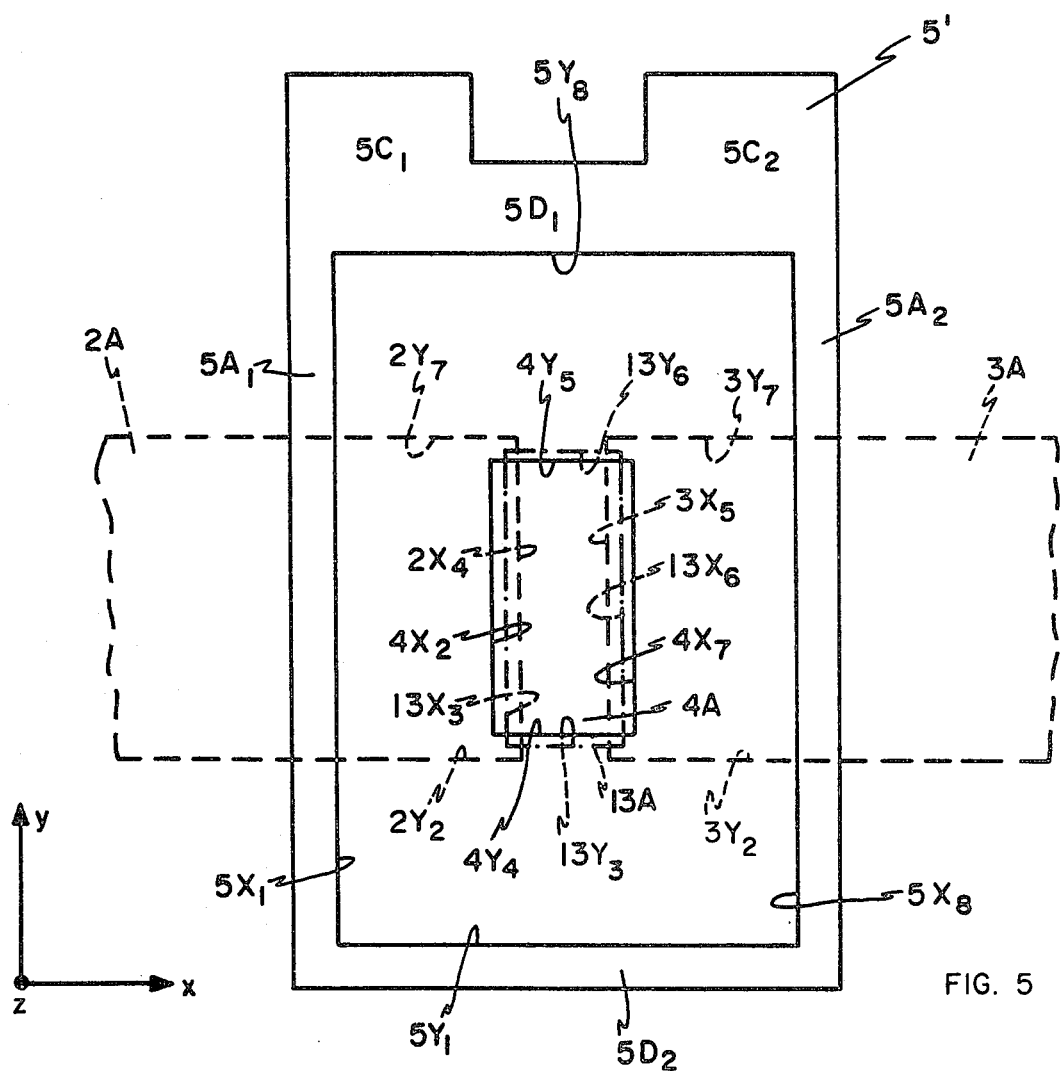
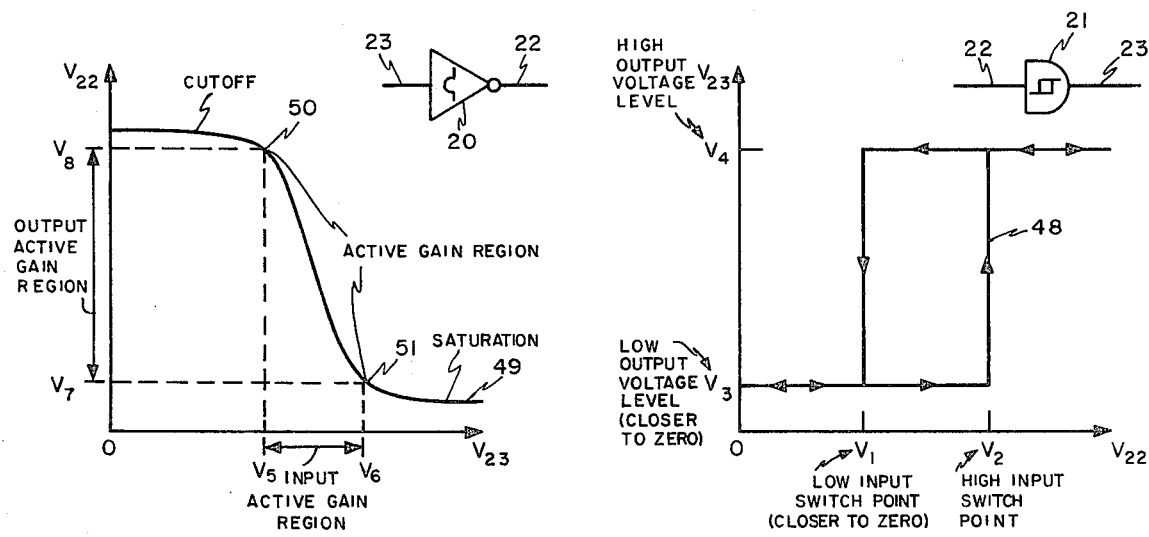
FIG. 7
FIG. 8

OSCILLATOR THAT INCLUDES A CHARGE-FLOW TRANSISTOR

The Government has rights in this invention pursuant to Grant No. ENG-7717219 awarded by the National Science Foundation.

The present invention relates to oscillators that include charge-flow transistors.

By way of background, attention is called to the following Letters Patent and applications therefor assigned to the Massachusetts Institute of Technology: U.S. Pat. No. 4,158,807 (Senturia); U.S. Pat. No. 4,209,796 (Senturia); U.S. Pat. No. 4,236,121 (Senturia); and Ser. No. 076,037, filed Sept. 17, 1979 (Senturia). One embodiment of the oscillator herein disclosed employs as one vital element thereof charge-flow transistors of the type disclosed in the accompanying Senturia application which discloses devices that are the sole invention of the inventor Senturia herein; indeed, two figures hereof, as later discussed, are the same as figures in the accompanying Senturia application and are included to satisfy the requirements of the Patent Act.

A charge-flow transistor (CFT) of the type described in the above-identified patent and patent applications is a field effect device in which the gate thereof is formed of conductive fingers with a gap material (also called "gate material" herein) between the fingers. The gap material has some electrical conductance but its conductance is much less than the conductance of the conductive fingers. The conductance of the gap material and, hence, information on the conduction process in the gap material, can be inferred, as noted in said U.S. Pat. No. 4,158,807, from the electrical characteristics of the device. The electrical device characteristics may be measured or monitored to note changes in the conductance of the gap material that arise from changes in the environment in which the charge-flow transistor is located, for example, to sense smoke, humidity, temperature and changes therein or other environmental conditions which affect the conduction process (and hence the conductance) of the gap material. Alternatively, such changes in conductance may arise from physical processes, such as chemical reactions that may take place within the gap material. In either event, such changes in conductance can be bulk conductance changes or surface conductance changes.

Typically, when the CFT is functioning as a sensor of a condition of the environment around that CFT, the gap material should be a thin film to reduce the time needed for the transistor to react to changes in that environment, as well as to increase the magnitude of reaction within the CFT. This is so because the CFT senses effects in the electrically sensitive region or channel region thereof, as later discussed in some detail; those effects at the electrically sensitive region, in turn, are occasioned by charge distribution at or near the interface between the gap material and the gate insulator of the CFT and the charge distribution is affected by changes in the conductance of the gap material. A thin film generally permits faster (and greater) reaction on the part of the CFT.

On the other hand, if it is a condition of the gap material itself that is to be detected, then the gap material need not, and often preferably will not, be a thin film. Such condition might, for example, be a chemical reaction occurring in the gap material, wherein the rate at which the chemical reaction progresses might be important.

Thus, the gap material of a charge-flow transistor has the function of modifying electric current in the charge-flow transistor between the source and drain thereof, and the current flow, in turn, typically, is sensed and analyzed to derive information with respect to the material in the gap as well as the characteristics of the environment within which the material is located. An object of the present invention is to provide a simplified oscillator circuit for monitoring electric current flow in a charge-flow transistor.

Another object is to provide an oscillator that minimizes circuit parts but which is, nevertheless, stable, accurate and sensitive.

These and still further objects are addressed hereinafter.

The foregoing objects are achieved, generally, in an oscillator that comprises, in combination, an inverter logic element comprising the combination of a charge-flow transistor and a load element, and a Schmitt trigger or the like connected to receive as input the output of the logic element and to provide an output which is fed back as input to the logic element. The Schmitt trigger is operable in response to the input thereto to effect periodic TURN-ON and TURN-OFF of the logic element. The period of oscillation of the oscillator is dominated by the conductance of the gap (or gate) material of the charge-flow transistor. Many gap materials that are useful for such charge-flow transistors exhibit charge storage or build-up which can deleteriously affect oscillations. The oscillator of the present invention is adapted to provide stable oscillations despite changes in charge storage which would otherwise adversely affect such oscillations. Also, the Schmitt trigger or the like, for there to be oscillations, must be operable, in response to the input thereto from the inverter logic element, to effect periodic TURN-ON and TURN-OFF of the inverter logic element.

The invention is herein after described with reference to the accompanying drawing in which:

FIG. 5 is a partial plan view, greatly enlarged, of a portion of the charge-flow transistor of FIG. 4;

FIG. 7 shows a static transfer characteristic for a charge-flow transistor; and

FIG. 8 shows a transfer characteristic for a Schmitt trigger.

Figure 1A:
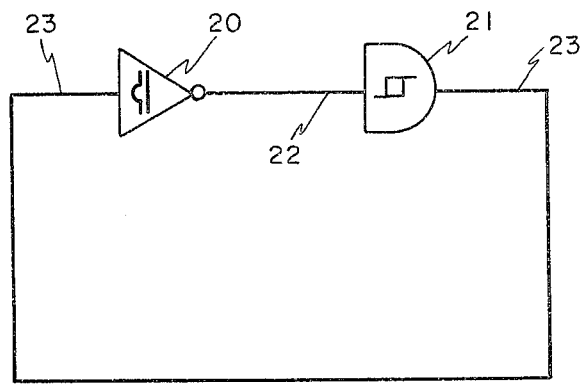
FIG. 1A is a diagrammatic representation of a circuit embodying the present inventive concepts.

Turning now to FIG. 1A, an oscillator 102 is shown consisting of an inverter logic element 20 and a Schmitt trigger 21 interconnected in a circuit. A Schmitt trigger, as is known, is a non-inverting logic element with hysteresis. The Schmitt trigger 21 is connected to receive as input at 22 the output of the logic element 20 and to provide an output at 23 which is fed back as input to the logic circuit 20. Later it is shown that the level of the voltage fed back from the Schmitt trigger 21 to the inverter 20 can be quite important. Thus, the oscillator labeled 102A in FIG. 1B includes a level shifter 25 which is discussed later. Of course, the level shifting function can be incorporated in the Schmitt trigger 21 in FIG. 1A.

Figure 3:
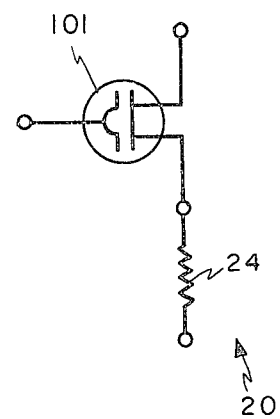
FIG. 3 is a schematic representation of one element in the circuits of FIGS. 1A and 1B, employing a charge-flow transistor.
Figure 4:
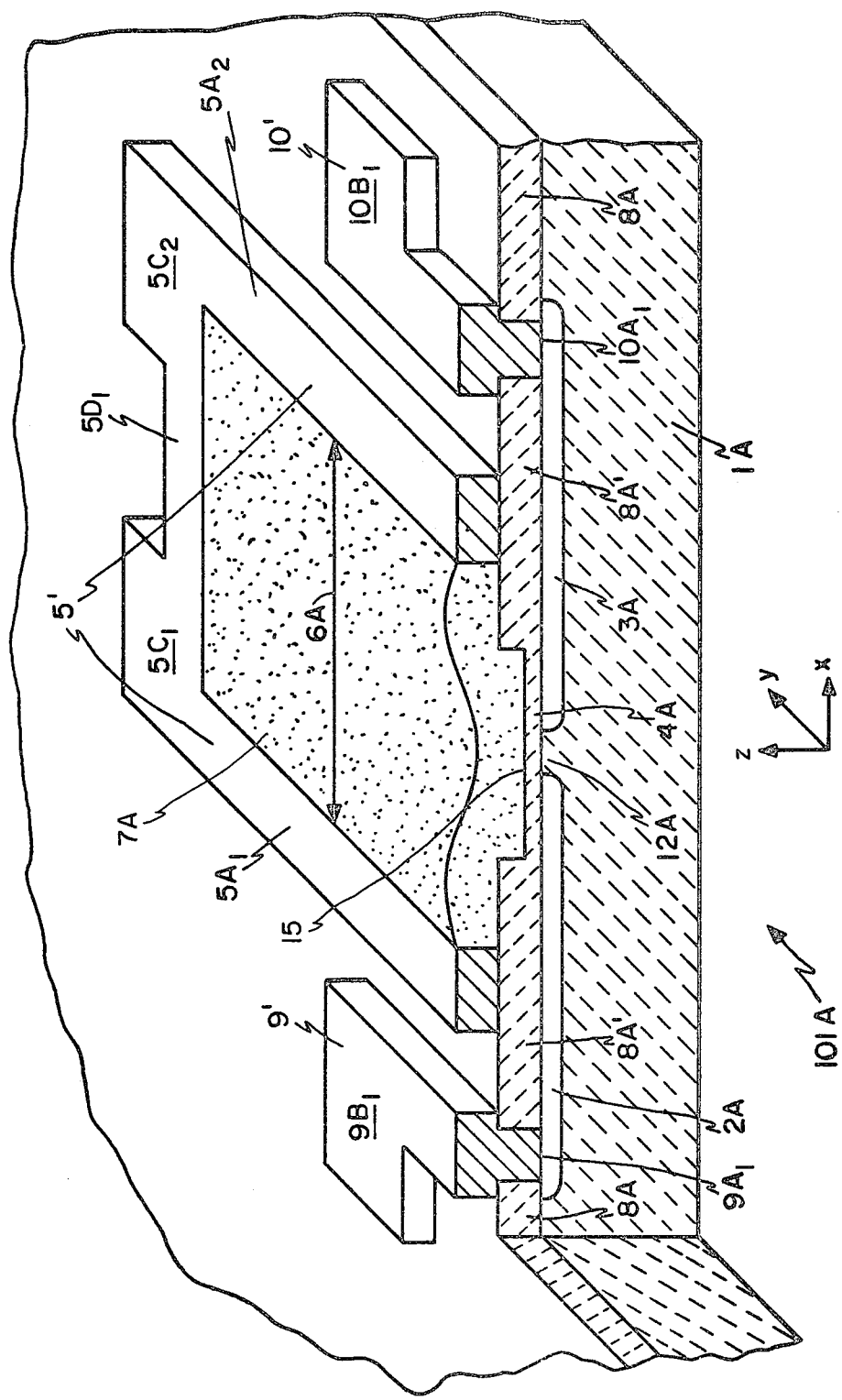
FIG. 4 is an isometric view, greatly enlarged and partly cutaway, of one form of the charge-flow transistor shown schematically in FIG. 3.

The logic element 20, as shown in FIG. 3, consists of a charge-flow transistor 101 and a load element (e.g., a resistor) 24. One form the charge-flow transistor 101 can take is that shown at 101A in FIG. 4. The charge-flow transistor 101A, as shown in FIG. 4, comprises a semiconductor substrate 1A, a source region 2A, a drain region 3A, a gate insulator 4A, a gapped gate electrode 5' comprising a pair of conductive fingers $5A_1$ and $5A_2$ with a gap 6A between the fingers. A gap material 7A having some conductance is disposed within the gap 6A. The conductance of the gap material 7A is much less than the conductance of the fingers $5A_1$ and $5A_2$. Typically, the fingers are formed of aluminum which is highly conductive and the gap material 7A may be taken from the group consisting of organic polymers, metal oxides, oxide glasses, metallo-inorganic compounds, chalcogenide glasses and other amorphous inorganic semiconductors, for example. All the foregoing gap materials have much lower conductance than that of the fingers. The electrical conductance of the gap material 7A expressed as a sheet conductance is typically greater than about $10^{-17}$ (ohms/square)$^{-1}$. Also, typically, the gap material 7A is a thin film $\sim 1000$ Å to 10,000 Å thick, but, for some uses, it need not be a thin film.

The device 101A is, of course, a small, flat semiconductor slab or wafer into which has been diffused impurities, to create the source region and the drain region. These regions are often fabricated in identical fashion and are, in such case, electrically equivalent as to function. The gate 5' can have a yoke $5D_1$ connecting the fingers $5A_1$ and $5A_2$ and the fingers can be connected together at their free ends (as shown in FIG. 5) to provide shielding (see said Patent 4,209,796). The upper surface of the slab is covered by thin insulators 8A and 8A', except for the portions thereof in electrical contact with a source contact $9A_1$ of a source electrode 9', a drain contact $10A_1$ of a drain electrode 10', and the gate insulator 4A which is disposed between the sensor material 7A and the substrate 1A. Pads $9B_1$, $5C_1$ and $5C_2$, and $10B_1$ permit electrical contact to the source, gate and drain, respectively, of the device 101A, as is well known. The pads are isolated from the substrate by the insulating layers 8A and 8A' which serve to insulate the contacts or electrodes 5', 9' and 10' from the substrate and from each other. The gate insulator 4A can be a thin silicon dioxide layer. The insulators 8A and 8A' can also be a silicon dioxide layer but must be thicker than gate insulator 4A. Throughout this explanation, the terms "source" and "drain" are used to designate the electrical connection to the source region of the charge-flow transistor and the drain region thereof, respectively, as is done with respect to conventional MOS devices, as well as the respective region. The term "gate" is employed in its usual context.

There is a detailed explanation in said U.S. Pat. No. 4,158,807 of the various forms that the charge-flow transistor can take: it may be an enhancement mode p-channel device in which there is no conduction in the electrically sensitive region or channel region labeled 12A in the absence of an appropriate bias; or it may be a depletion mode n-channel device in which there is no conduction in the electrically sensitive region or channel region 12A in the presence of an appropriate bias. Herein the explanation is directed to the structure to apply the appropriate bias to the device, rather than the precise type of device used, that is, whether electrons or holes provide current flow in the region 12A or whether the device be an enhancement or depletion mode type. It should be noted at this juncture that the electrically sensitive region or channel region 12A when the transistor 101A is biased ON is known as a channel; also biasing is achieved by virtue of an electric field through the gate insulator 4A (in the z-direction in FIG. 4) by virtue of charge carrier distribution in the gap material 7A at and around the interface shown at 15 between the gap material 7A and the gate insulator 4A.

Because the relative positions of the boundaries of various regions are critical to the description (and operation) of the device, there is shown in FIG. 5 an enlarged plan-view of a portion of the charge-flow transistor 101A of FIG. 4, in which the gap material 7A has been omitted, but which includes a sampling electrode 13A and a second connective yoke $5D_2$, not shown in FIG. 4. The extent of the electrically sensitive region, i.e., the channel region 12A, can be described with reference to FIG. 5. The boundaries of the electrically sensitive region are that edge of the source region 2A denoted $2X_4$, the projection into the substrate of those edges of the gate insulator 4A denoted by $4Y_4$ and $4Y_5$, and that edge of the drain region 3A denoted by $3X_5$.

The connective yokes $5D_1$ and $5D_2$ provide electrical connection between the gate fingers $5A_1$ and $5A_2$ and serve to shield the electrically sensitive region, as described in said Ser. No. 853,059. The critical relative locations of features of the device can be described as follows. With reference to the x-axis shown in FIG. 5, the relative order of the x positions (i.e., positions in the x-direction from left to right) of the labeled edges is: that edge of the gate finger $5A_1$ denoted by $5X_1$; said gate insulator edge $4X_2$; said source region edge $2X_4$; said drain region edge $3X_5$; said gate insulator edge $4X_7$; and that edge of gate finger $5A_2$ denoted $5X_8$. With reference to the y-axis shown in FIG. 5, the relative order of the y positions (i.e., the positions in the y-direction from bottom toward the top in FIG. 5) of the labeled edges is: in any order, that edge of the yoke $5D_2$ denoted by $5Y_1$, that edge of the source region 2A denoted $2Y_2$, and that edge of drain region 3A denoted $3Y_2$; said gate insulator edge $4Y_4$; said gate insulator edge $4Y_5$; and, in any order, that edge of the source region 2A denoted $2Y_7$, that edge of drain region 3A denoted by $3Y_7$, and that edge of gate electrode 5' denoted $5Y_8$. In some embodiments of the present invention, it may be useful to add a sampling electrode 13A (shown in broken-line form in FIG. 5), comprising a highly conductive island pad sandwiched between gate insulator 4A and gap material 7A of FIG. 4. The x- and y-positions of the boundaries of such a sampling electrode are shown at $13X_3$, $13Y_6$, $13x_6$, and $13Y_3$ in FIG. 5. The positions of these edges relative to the other designated edges are not critical. Those positions shown in FIG. 5, namely $13Y_3$ and $13Y_6$ outside the boundaries $4Y_4$ and $4Y_5$, respectively, assure that electric field between the gap material 4A and the electrically sensitive region 12A is made uniform across the entire electrically sensitive region 12A by the presence of sampling electrode 13A, a property that is useful in quantitative studies of conductive processes and bias changes in gap material. It should be further noted that any charge carrier movement between the sampling electrode 13A and the gate electrode 5' is through or on the gap material 7A.

The gap material 7A in FIG. 4 is electrically connected with the gapped gate electrode 5' in order to permit charge-flow in the gap material 7A to control electric current flow in the electrically sensitive region or channel region 12A. It is noted above that the gap material 7A is only weakly conducting (typically the electrical conductance of gap material, expressed in sheet conductance, is greater than about $10^{-17}$ (ohm/square)$^{-1}$ with an upper limit of electrical conductance at about $10^{-6}$ (ohms/square)$^{-1}$, whereas the fingers $5A_1$ and $5A_2$ may be aluminum which is highly conducting. In this situation, a voltage applied to the fingers $5A_1$ and $5A_2$ will evoke charge flow across or through the gap material 7A, which charge flow serves to bias the device 101A. The rate at which such charge flow progresses from the fingers $5A_1$ and $5A_2$ to the part of the gap material 7A at the opposite side of the gate insulator 4A from the electrically sensitive region or channel region 12A is a function of the electrical properties of the gap material; and those electrical properties are a function of the inherent electrical characteristics of the gap material and the effect of the environment thereon. The electrical properties of the material 7A primarily determine TURN-ON ("$t_{on}$" herein) of the device 101A. However, when the fingers $5A_1$ and $5A_2$ are outside the electrically sensitive region or channel region 12A, as they are in the device 101A, then the electrical properties of the gap material primarily also determine the TURN-OFF time ("$t_{off}$" herein) of the device 101A, and, indeed, in the device 101A $t_{on} \sim t_{off}$, that is, $t_{on}$ and $t_{off}$ are about within an order of magnitude of each other. Said another way, no part of the highly conductive portions of the gate 5' (i.e., the fingers $5A_1$ and $5A_2$ and the conductive yokes $5D_1$ and $5D_2$ connecting the free ends of the fingers $5A_1$ and $5A_2$ which typically are aluminum patterns at the surface of the transistor) overlap the electrically sensitive region or channel region 12A. A CFT without the yokes $5D_1$ and $5D_2$ can also be employed, which permits individual biasing of the fingers $5A_1$ and $5A_2$. In such a case, the finger $5A_1$ is contacted through the pad $5C_1$ of FIG. 4 and the finger $5A_2$ is contacted through the contact pad $5C_2$ of FIG. 4. The times $t_{on}$ and $t_{off}$ both depend upon the charge flow process in the gap material 7A and that process is much slower than the relatively rapid conduction of charge in semiconductors and metals in conventional FET devices; thus, time delays occasioned by $t_{on}$ and $t_{off}$ are much longer than time delays present in the rest of the oscillator circuit.

With the exception of the techniques for fabricating the gapped gate electrode filled with a thin-film or other gap material 7A, the fabrication procedures for n-channel and p-channel charge-flow transistors and for enhancement-mode and depletion mode charge-flow transistors are based on well-established art, using many of the same techniques widely used in the manufacture of MOSFETs (metal-oxide-semiconductor field-effect transistors) and MOS integrated circuits, as is discussed in said U.S. Pat. No. 4,158,807.

Figure 6:
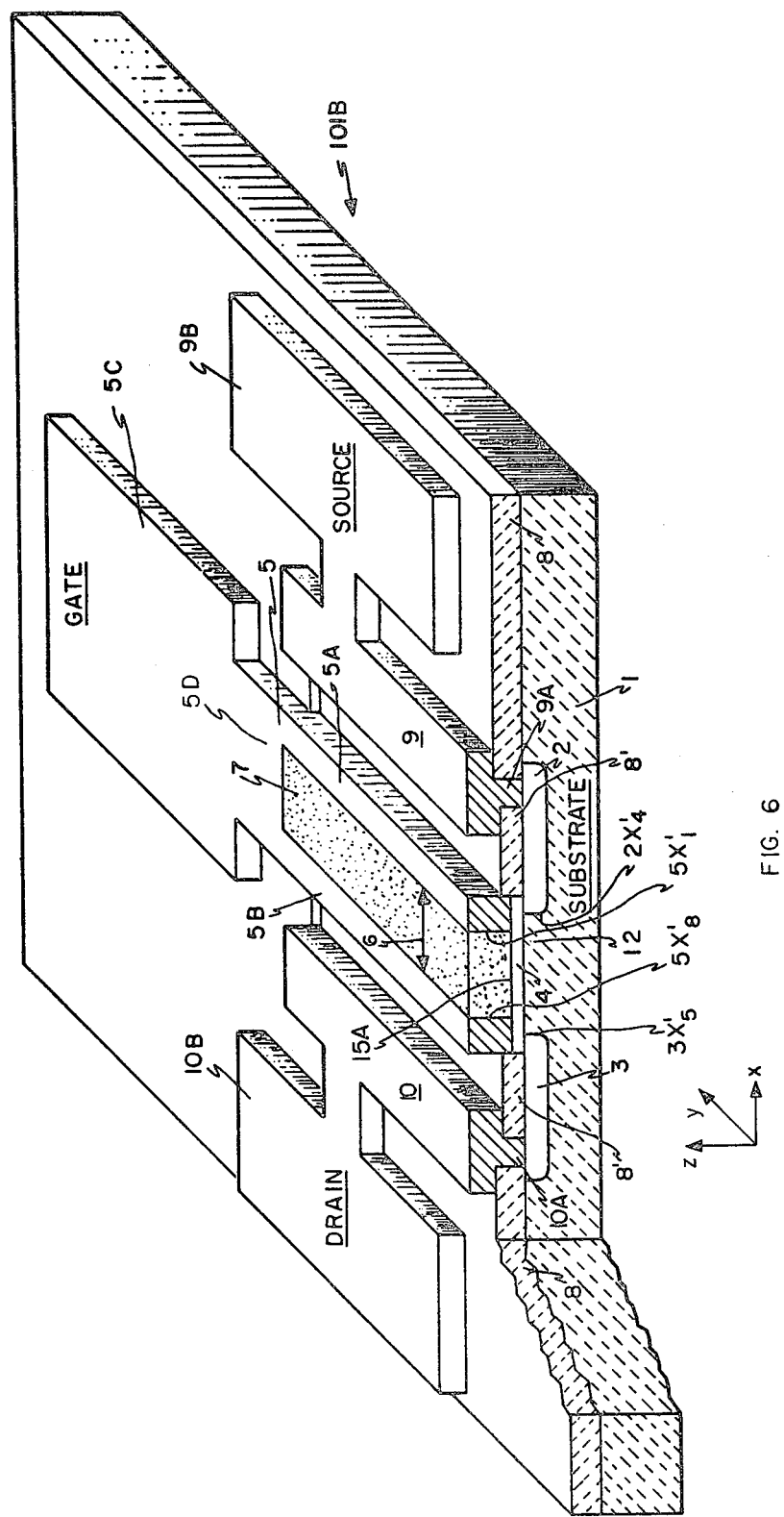
FIG. 6 is an isometric view, greatly enlarged and partly cutaway, of another form of the charge-flow transistor shown schematically in FIG. 3.

Transistors such as the transistor 101A are monitored by measuring electric current flow i.e. current flow in the electrically sensitive region or channel region 12A. That electric current flow, as above indicated, is controlled by an electric bias field applied through the gate insulator 4A, and the bias field, in turn, is controlled by charge flow in the gap material 7A. As is noted previously herein, when a CFT is conducting, the channel region 12A is known as a channel. It is, then, the current flow in the channel 12A which is monitored. That monitoring can be effected in a more or less dc mode, but usually it is not. In the system herein described monitoring is ac monitoring; more precisely, the CFT is placed in the context of a logic element (e.g., the logic element 20 in FIG. 3) and that logic element is made part of an oscillator that further includes a Schmitt trigger to provide the oscillator 102 in FIG. 1. The frequency of oscillation (i.e., 1/period) in an oscillator 102 in which the CFT is like 101A in FIG. 4 is a function of both $t_{on}$ and $t_{off}$ of the CFT, whereas the frequency of oscillation in an oscillator 102 in which the CFT is like that shown at 101B in FIG. 6 is dominated by the TURN-ON time $t_{on}$ thereof since the relationship between $t_{on}$ and $t_{off}$ of the charge-flow transistor 101B is $t_{on} \gg t_{off}$.

In either event, however, there are a number of important factors that should be explained about the oscillator 102 in FIG. 1A, whether the CFT in the logic element 20 be like 101A or 101B. The oscillator 102 contains a Schmitt trigger, i.e., a device whose transfer characteristic exhibits hysteresis; see FIG. 8. The charge-flow transistor (whether 101A or 101B) presents time delays (i.e., $t_{on}$ and, sometime, $t_{off}$) between the switching of the Schmitt trigger output 23 (which is also the input to the inverter 20) in FIG. 1A and the resulting change of state of the inverter output 22 (which is also the input to the Schmitt trigger 21) to that value corresponding to the input to the inverter 20. The values of $t_{on}$ and $t_{off}$ of the transistor 101A can range from milliseconds to hundreds of seconds, depending on the environment that affects the particular material being used, the geometry of the gate, and so forth; and both times $t_{on}$ and $t_{off}$ typically will vary as a function if the conductance of the material 7A, as above discussed. Hence, the frequency of oscillation of the oscillator 102 with a CFT 101A is a function of both $t_{on}$ and $t_{off}$ and an instrument taking that fact into consideration can be employed to relate oscillation frequency to the conductance and, thence, to an environmental condition. Similar remarks apply to an oscillator embodying a CFT like the CFT 101B except that it is the time $t_{on}$ that is important there. A number of critical relationships between the CFT in the inverter 20 and the Schmitt trigger 21 are now discussed with reference to FIGS. 7 and 8.

The Schmitt trigger 21 in FIG. 1 has two input switch points (i.e., the voltages designated $v_1$ and $v_2$ on the Schmitt trigger transfer characteristic marked 48 in FIG. 8) and two output voltage levels (i.e., the voltage levels marked $v_3$ and $v_4$); both the switch points $v_1$ and $v_2$ must be in the inverter output active gain region in FIG. 7, that is, between points 50 and 51 on the static transfer characteristic labelled 49 of the inverter logic element 20. Also the Schmitt trigger must have a range of voltages between the two output voltage levels $v_3$ and $v_4$ in FIG. 8, which overlap the inverter input active gain region, that is, the range of the voltages between $v_3$ and $v_4$ must overlap the range of voltages between $v_5$ and $v_6$ in FIG. 7. (The designations $v_{22}$ and $v_{23}$ in FIGS. 7 and 8 indicate voltages that appear at conductors 22 and 23, respectively, in FIG. 1A.) One further matter should be addressed at this juncture.

The voltages $v_1$–$v_8$ may be plus (+) voltages or minus (−) voltages depending on the channel type and device mode (depletion or enhancement). The terms "high" and "low", then, in FIG. 8 relate to absolute values of voltage.

Thus, in order that the oscillator function properly the Schmitt trigger transfer characteristics must be matched to the CFT transfer characteristics so as to provide voltages in the ranges above noted. A Schmitt trigger can be built to give the required ranges; or the level shifter 25 can be provided.

Figure 1B:
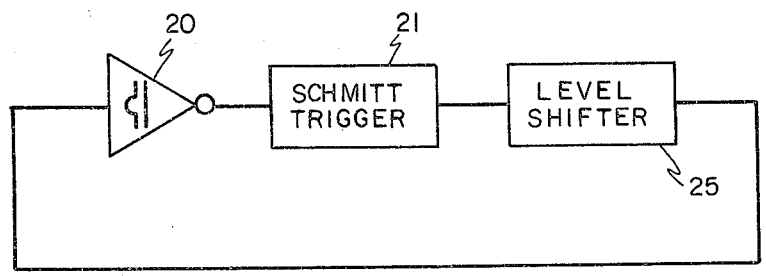
FIG. 1B is a diagrammatic representation of a modification of the circuit of FIG. 1A.
Figure 2:
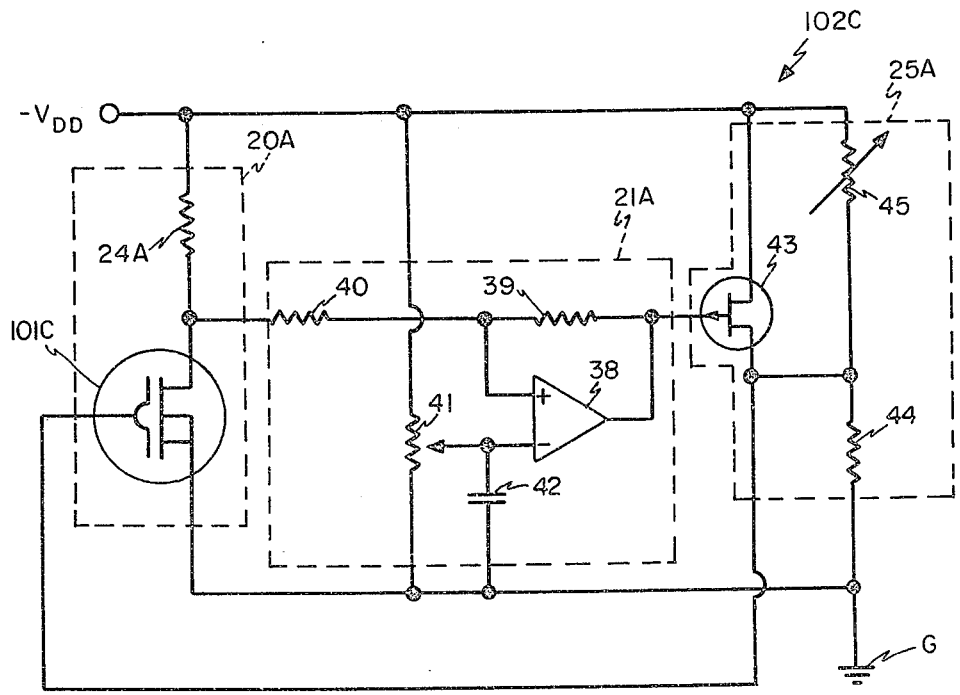
FIG. 2 is a schematic diagram showing an implementation of the circuit of FIG. 1B.

The oscillator marked 102C in FIG. 2 shows schematically one form the circuit of FIG. 1B can take. The oscillator 102C comprises an inverter 20A, a Schmitt trigger 21A and a level shifter 25A. The inverter 20A consists of a charge-flow transistor 101C and resistor 24A; the Schmitt trigger 21A consists of an amplifier 38, resistors 39 and 40, a potentiometer 41 and a stabilizing capacitor 42; and the level shifter 25A consists of an FET 43, a resistor 44 and a variable resistor 45. Power is connected to the oscillator 102C between $V_{DD}$ and ground.

A later circuit was built which differed from that in FIG. 2 in that the voltage level shifting function was built into the Schmitt trigger, and all components were fabricated as a monolithic integrated circuit. The integrated circuit thus built had a polymer poly (p-aminophenylacetylene) as gap material. The frequency of oscillation varied as a function of relative humidity.

The oscillator above described is very stable, particularly since it is possible to set the switch points of the Schmitt trigger to points where charge storage, found in CFTs employing certain gap materials, is stable, so that the oscillator thus fabricated is stable despite such charge storage. The oscillator employs a single inverter logic element and a single Schmitt trigger which reduces the number of circuit elements and cost thereof; and those circuit elements can be fabricated using monolithic integrated circuit techniques, as just noted.

Work done by the present inventors to date indicates that the transistor 101A has characteristics which tend to favor its structure for use in the oscillators 102 or 102A or 102C, but the charge-flow transistor 101B in FIG. 6 can also be employed. The transistor 101B will be recognized as the charge-flow transistor disclosed in said U.S. Pat. No. 4,158,807, comprising a semi-conductor substrate 1, a source region 2, a drain region 3, a gate insulator 4, and a gapped gate electrode 5 comprising a pair of fingers 5A and 5B with a gap 6 between the fingers. A gap material (or gate material) 7, like the gap material 7A, is disposed in the gap 6 and electrically connected with the gapped gate electrode 5 to permit charge flow in the gap material to control current flow in the substrate in the electrically sensitive region or channel region labeled 12 adjacent the gate insulator 4, between the source region 2 and the drain region 3. The interface between the gap material 7 and the gate insulator 4 is marked 15A. The gate 5 consists of the fingers 5A and 5B electrically interconnected by a yoke 5D; another yoke (like the yoke $5D_2'$ in FIG. 5) can be provided to achieve shielding as discussed in said U.S. Pat. No. 4,209,796.

Whereas, in the case of the transistor 101A, no portions of the conductive fingers or any other conductive portion of the gate electrode overlap the electrically sensitive region 12A (thereby providing a charge-flow transistor whose TURN-ON time $t_{on}$ is of a comparable order of magnitude to the TURN-OFF time $t_{off}$ thereof), in the case of the transistor 101B in FIG. 6, the conductive fingers 5A and 5B do in fact overlap the electrically sensitive region 12; hence, the transistor 101B has a TURN-ON time $t_{on}$ that is determined primarily by the electrical properties of the gap material 7, but $t_{off}$ is not. Thus, as to the transistor 101B, $t_{on} \gg t_{off}$ ($t_{on}$ being in the range from milliseconds to hundreds of seconds whereas $t_{off}$ is typically less than a microsecond).

The explanation made previously with reference to FIG. 5 as applied to the transistor 101A can be used as to the transistor 101B with appropriate changes. First, of course, the transistor 101B does not have a electrode like the sampling electrode 13A in FIG. 5. In FIG. 6 the labels $2X_4'$, $5X_4'$, $5X_8'$ and $3X_5'$ (which correspond to $2X_4$, $5X_1$, $5X_8$ and $3X_5$, respectively, in FIG. 5) indicate the inner edge of the highly conductive finger 5A, the edge of the source 2 (i.e., the right boundary of the electrically sensitive region or channel region 12), the inner edge of the highly conductive finger 5B and the edge of the 3 (i.e., the left boundary of the electrically sensitive region or channel region 12). The other boundaries in FIG. 5 can apply also to the transistor 101B in FIG. 6. It can be seen then, that the highly conductive fingers 5A and 5B in FIG. 6 overlap the electrically sensitive region 12; and, as to the transistor 101B, $t_{on} \gg t_{off}$.

Although Schmitt trigger have been found to be best for present purposes, other circuit means could be used that include, for example, circuit elements with incremental negative resistance characteristics.

Further modifications of the invention herein disclosed will occur to persons skilled in the art and all such modifications are deemed to be within the scope of the invention as defined by the appended claims.

What is claimed is:

1. An oscillator that comprises, in combination, an inverter logic element comprising the combination of a charge-flow transistor and a load element, and a Schmitt trigger connected to receive as input the output of the logic element and to provide an output which is fed back as input to the logic element, said Schmitt trigger being operable in response to the input thereto to provide periodic TURN-ON and TURN-OFF of the logic element, said charge flow transistor comprising: a semiconductor substrate, having formed therein a source region and a drain region, the source and drain regions being situated in the substrate such that a sensitive channel region separates them from each other; a gate insulator situated above the sensitive channel region of the substrate; and a gate means comprising high conductive member situated far enough remote from the channel region so that charge thereon does not directly affect the channel region and a gate material having some conductance electrically connected with said highly conductive member to permit charge-flow therebetween, whereby when a charge is applied to the highly conductive member, current will flow in the channel at a rate dependent on the impedance of the material, said charge flow transistor being operable to cause inversion and to provide a circuit delay in which the TURN-ON and TURN-OFF time are of comparable orders of magnitude.

2. An oscillator as claimed in claim 1 in which the gate means comprising a pair of conductive fingers with a gap between the fingers and a gap material having some electrical conductance disposed in said gap and electrically connected with the conductive fingers to permit charge flow in the gap material to control electric current flow in the electrically sensitive region in the substrate, the gate means being positioned such that no part of the conductive portions thereof overlaps the electrically sensitive region of the transistor.

3. An oscillator as claimed in claim 2 in which both the TURN-ON time $t_{on}$ of the charge-flow transistor and the TURN-OFF time $t_{off}$ thereof are determined primarily by electrical properties of the gap material which acts to control electric current flow in said electrically sensitive region.

4. An oscillator as claimed in claim 2 in which the Schmitt trigger has two input switch points $v_1$ and $v_2$ and two output voltage levels $v_3$ and $v_4$, both of the switch points $v_1$ and $v_2$ being in the inverter output active gain region between voltage levels $v_7$ and $v_8$ of the inverter transfer characteristic of the inverter logic element and a range of voltages between the two output voltage levels $v_3$ and $v_4$ which overlaps the inverter input active gain region.

5. An oscillator as claimed in claim 4 wherein that further includes a voltage level shifter connected between the output of the Schmitt trigger and the input to the inverter to provide appropriate voltages $v_1$, $v_2$, $v_3$ and $v_4$.

6. An oscillator as claimed in claim 1 in which the gate means comprising a pair of conductive fingers with a gap between the fingers and a gap material having some electrical conductance disposed in said gap and electrically connected with the conductive fingers to permit charge-flow in the gap material to control electric current flow in the electrically sensitive region in the substrate, and a gate insulator adjacent the electrically sensitive region in the substrate between the source region and the drain region and sandwiched between the both gap material and the conductive fingers and the electrically sensitive region of the substrate, said electrically sensitive region being electrically sensitive to any electric field bias applied through the gate insulator.

7. An oscillator as claimed in claim 6 in which the Schmitt trigger has two input switch points and two output voltage levels, both switch points being in the inverter output active gain region of the inverter transfer characteristic of the inverter logic element and having a range of voltages between the two output voltage levels of the Schmitt trigger which overlaps the inverter input active gain region.

8. An oscillator that comprises: a logic element having, in combination, a charge-flow transistor comprising a semiconductor substrate, a source region, a drain region, an electrically sensitive region in the semiconductor substrate separating the source region from the drain region, gate means comprising a highly conductive member and a gate material having some conductance electrically connected with said highly conductive member to permit charge-flow therebetween, the conductance of the gate material being much less than the conductance of said highly conductive member, a gate insulator sandwiched between the gate material and said electrically sensitive region, said electrically sensitive region being sensitive to any bias electric field applied through the gate insulator, said logic element further including a load element connected to one of the source region and the drain region of the charge-flow transistor; and a non-inverting Schmitt trigger logic circuit with hysteresis connected to receive as input an output from the logic element and provide an output fed back as input to the logic element said non-inverting logic circuit being operable in response to the input thereto to effect periodic TURN-ON and TURN-OFF of the logic element, and said charge-flow transistor being operable to cause inversion and to provide a circuit delay in which the TURN-ON time and TURN-OFF time are of comparable orders of magnitude.

9. An oscillator as claimed in claim 8 in which no part of said highly conductive member overlaps said electrically sensitive region so that said bias electric field is created in said charge-flow transistor substantially totally by charge patterns in the gate material at and near the interface between the gate material and the gate insulator, to provide a charge-flow transistor having a TURN-ON time $t_{on}$ that is about equal to the TURN-OFF $t_{off}$ thereof.

10. An oscillator having, in combination: an inverter logic element comprising the combination of a charge-flow transistor and a load element; and a non-inverting Schmitt trigger logic circuit with hysteresis connected to receive as input an output from the inverter logic element and to provide an output fed back as input to the inverter logic element, said non-inverting logic circuit being operable in response to the input thereto from the inverter logic element to effect periodic TURN-ON and TURN-OFF of the inverter logic element to provide oscillations, said charge flow transistor comprising: a semiconductor substrate, having formed therein a source region and a drain region, the source and drain regions being situated in the substrate such that a sensitive channel region separates them from each other; a gate insulator situated above the sensitive channel region of the substrate; and a gate means comprising a high conductive member situated far enough remote from the channel region so that charge thereon does not directly affect the channel region and a gate material having some conductance electrically connected with said highly conductive member to permit charge-flow therebetween, whereby when a charge is applied to the highly conductive member, current will flow in the channel at a rate dependent on the impedance of the material, said charge flow transistor being operable to cause inversion and to provide a circuit delay in which the TURN-ON and TURN-OFF time are of comparable orders of magnitude.

11. An oscillator having, in combination: a single inverter logic element comprising the combination of a charge-flow transistor and a load element; and Schmitt trigger circuit means connected to receive as input the output of the single inverter logic element and having an output connected as input to the single inverter logic element, said circuit means being operable in response to the input thereto from the single inverter logic element to effect periodic TURN-ON and TURN-OFF of the single inverter logic element to provide oscillations, said charge flow transistor comprising: a semiconductor substrate, having formed therein a souce region and a drain region, the source and drain regions being situated in the substrate such that a sensitive channel region separates them from each other; a gate insulator situated above the sensitive channel region of the substrate; and a gate means comprising a high conductive member situated far enough remote from the channel region so that charge thereon does not directly affect the channel region and a gate material having some conductance electrically connected with said highly conductive member to permit charge-flow therebetween, whereby when a charge is applied to the highly conductive member, current will flow in the channel at a rate dependent on the impedance of the material, said charge-flow transistor being operable to cause inversion and to provide a circuit delay in which the TURN-ON and TURN-OFF time are of comparable orders of magnitude.

12. An oscillator that includes the combination of an inverter logic element and Schmitt trigger means operable to effect periodic TURN-ON and TURN-OFF of the inverter logic element, said inverter logic elemnt comprising a charge-flow transistor and a load element interconnected, said means operable being connected to receive as input the output of the inverter logic element, said charge-flow transistor comprising a semiconductor substrate, a source region in the substrate, a drain region in the substrate, an electrically sensitive region in the substrate between the source region and the drain region, gate means comprising a highly conductive member and a gate material having much less conductance than the highly conductive member, said gate material being electrically connected to the highly conductive member to permit charge-flow therebetween, a gate insulator sandwiched between the gate material and the electrically sensitive region of the substrate, the electrically sensitive region being sensitive to any bias electric field applied through the gate insulator, said bias electric field being created in the charge-flow transistor substantially totally by charge patterns in the gate material in the part thereof adjacent the gate insulator, no part of said highly conductive member of the gate means being in overlap of said electrically sensitive region to provide a transistor whose TURN-ON time $t_{on}$ is within about an order of magnitude of its TURN-OFF time $t_{off}$, both the time $t_{on}$ and the time $t_{off}$ presenting time delays which affect the period of oscillation of the oscillator, which time delays are a function of charge flow in or on the gate material and are much longer than time delays present in the rest of the oscillator circuit.

13. An oscillator according to claim 2 wherein said charge-flow transistor further comprises a sampling electrode, comprising a highly conductive island pad sandwiched between the gate insulator and the gate material, positioned on the opposite side of the gate insulator from the electrically sensitive region, any charge carrier movement between the sampling electrode and the gate means being through or on the gate material.

14. An oscillator according to claim 8 wherein said charge-flow transistor further comprises a sampling electrode, comprising a highly conductive island pad sandwiched between the gate insulator and the gate material, positioned on the opposite side of the gate insulator from the electrically sensitive region, any charge carrier movement between the sampling electrode and the gate means being through or on the gate material.

* * * * *